United States Patent [19]
Chen et al.

[11] Patent Number: 5,827,186
[45] Date of Patent: Oct. 27, 1998

[54] METHOD AND PDT PROBE FOR MINIMIZING CT AND MRI IMAGE ARTIFACTS

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 827,832

[22] Filed: Apr. 11, 1997

[51] Int. Cl.⁶ ............................................. A61B 5/05
[52] U.S. Cl. ...................... 600/407; 600/411; 600/427; 604/20; 607/92; 606/14
[58] Field of Search .................. 604/19–21; 600/407, 600/410, 421, 422, 425, 411, 427; 607/88, 89, 92; 606/14–17

[56] References Cited

U.S. PATENT DOCUMENTS

| | | | |
|---|---|---|---|
| 4,686,964 | 8/1987 | Yunoki et al. | 128/4 |
| 5,505,726 | 4/1996 | Meserol | 606/9 |
| 5,571,152 | 11/1996 | Chen et al. | 607/92 |
| 5,621,780 | 4/1997 | Smith et al. | 378/65 |
| 5,698,866 | 12/1997 | Doiron et al. | 257/99 |

OTHER PUBLICATIONS

Galvin, Electrically active polymers and their application, JOM, vol. 49, No. 3, pp. 52–55, Mar. 1997.

Saunders et al., Micrelectronic devices based on conductive polymers, Conference Title: 6th International Sampe Electronics Conference, v 6, pp. 449–458, Corporate Source, Westinghouse Science and Technology Cent, Pittsburgh, PA, Jun. 22, 1992.

*Primary Examiner*—Brian Casler
*Attorney, Agent, or Firm*—Ronald M. Anderson

[57] ABSTRACT

An implantable probe having a non-metallic insulating base, non-metallic conductive traces supported by the base, and a plurality of non-metallic light sources supported by the base and coupled to the conductive traces. The conductive traces and the light sources are fabricated from a conductive polymer, which does not cause any artifacts if the implantable probe is left at the treatment site while it is imaged. Further, the implantable probe includes an envelope that is transparent and hermetically encloses the base, the pair of conductive traces, and the light sources. At least a portion of the envelope is optically transparent, enabling light emitted by the light sources to illuminate an adjacent treatment site. The conductive traces and the base are substantially flexible, enabling the probe to be flexed without breaking when the implantable probe is advanced within the body to the treatment site. A non-metallic receiver coil implanted in a patient's body is energized by inductively coupling it to an external transmitter coil. The current from the receiver coil is conveyed to the implanted probe through non-metallic leads.

26 Claims, 8 Drawing Sheets

METHOD AND PDT PROBE FOR MINIMIZING CT AND MRI IMAGE ARTIFACTS

FIELD OF THE INVENTION

This invention generally relates to an implantable probe for administering light therapy, and more specifically, to an implantable probe used for treating sites that must be examined using computed tomography (CT), magnetic resonance imaging (MRI), or other imaging paradigms affected by metallic substances.

BACKGROUND OF THE INVENTION

The use of implantable probes for administering photodynamic therapy (PDT) is disclosed in commonly assigned U.S. Pat. No. 5,445,608, the disclosure and drawings of which are specifically incorporated herein by reference. As explained in this patent, abnormal tissue that has been absorbed with a photoreactive agent is destroyed by prolonged exposure to relatively low intensity light having a characteristic waveband that is substantially the same as an absorption waveband of the photoreactive agent. Since the photoreactive agent is preferentially absorbed by the abnormal tissue but not by surrounding normal tissue, only the abnormal tissue is affected by the PDT.

Several different embodiments of implantable probes are disclosed in the above-noted patent. Each of these probes includes metallic components and conductors. Radiologists and other medical practitioners familiar with medical imaging are aware that even very small metallic articles such as clips, surgical staples, and particles from metal drill bits used to remove bone can cause artifacts in MRI and CT images. These artifacts appear as "bright" spots in the images, which can seriously degrade the clarity of the images and the ability of a medical practitioner to evaluate the condition of body tissue. This problem can be particularly troubling if the artifacts overlie a known or suspected tumor site in a patient's body, since by obscuring the site, the artifact may make it impossible to evaluate the state of the medical treatment or the condition of the site.

Further, when PDT is administered to destroy a tumor, it is desirable to evaluate the efficacy of the treatment by imaging the treatment site using MRI or CT. However, artifacts in the images caused by the metallic components of the implantable probe can make it difficult to evaluate the progress of PDT in destroying abnormal tissue at the site in order to determine if treatment should be continued. The medical practitioner will thus be forced to use other techniques to determine the progress of the treatment. Ideally, it would be preferable to use an implantable probe for administering PDT that does not cause artifacts in the images produced using CT or MRI techniques.

When an MRI machine is employed for imaging a site, it produces strong magnetic fields that move any implanted medical device having components that are ferrous or otherwise attracted by a magnetic field. When such an implanted device is moved, injury or discomfort to a patient may occur. It would thus be preferable to employ an implanted medical device that is not affected by strong magnetic fields.

Recently, researchers have discovered a family of conducting polymers, which are non-metallic and have an electrical conductivity as much as 25 percent of that of copper metal. These conducting polymers are capable of carrying electrical currents on an ionic basis or by way of conjugated double bonds having mobile electrons. In addition to being much less biologically reactive than metals or semi-conductors, conducting polymers have several other useful characteristics, including: (1) low density/weight; (2) high elasticity; and (3) low cost. These characteristics have led to the development of numerous products that incorporate such polymers, including rechargeable batteries, aerospace components, anti-static coatings, electromagnetic shielding, flexible displays, self-darkening windows, medical devices, and various electronic components.

The creation of new polymeric products has been aided by the development of a light emitting diode (LED) composed of conducting polymers. Significantly, the wavelength (color) of the light produced by a polymeric LED is adjustable by varying the amplitude of the applied voltage. In contrast, only the intensity of the light produced by a non-polymeric LED can be adjusted by varying the applied voltage. Also, because the body of knowledge concerning conducting polymers is relatively new, and the exact physics of this family of polymers is not completely understood by the scientific community, the development of commercially viable products based on the polymeric LEDs has been slowed. For example, today, even the best polymeric LEDs can only provide illumination for a few hundred hours before it fails. In contrast, non-polymeric LEDs have a mean time between failure (MTBF) of several thousand hours. Although further research may be required to improve the usefulness of conducting polymers for fabricating LEDs for most applications, the short lifetime of these devices should not pose a problem in applications in which the devices must operate for a relatively short time. Accordingly, if used in a probe fabricated with polymeric conductors, the polymeric LEDs may be used to solve the artifact problem when imaging a treatment site at which the probe is disposed. This solution to the artifact problem in imaging is not disclosed or suggested by the prior art.

SUMMARY OF THE INVENTION

One aspect of the present invention is directed to an apparatus for administering a medical therapy to an internal treatment site disposed within a patient's body. The apparatus minimizes imaging artifacts in images that are produced in order to evaluate a condition of the treatment site following administration of the medical therapy. These images are made using computed tomography (CT), magnetic resonance imaging (MRI), or other imaging modalities. The apparatus includes a supporting structure comprising a non-metallic insulating base. A pair of non-metallic conductive traces and a non-metallic electronic component are supported by the base, and the electronic component is coupled to the conductive traces, which are adapted to connect to a power supply. The apparatus is encapsulated in an enclosure comprising a transparent, biocompatible material, and the enclosure, base, and conductive traces, all of which are substantially flexible.

The non-metallic electronic component can be an array of light sources on the base, which produces light employed for light therapy when energized by an electrical current from the power supply. The electronic component can include a light emitting device, such as an LED or an organic film.

Another aspect of the present invention is directed to a method for providing a medical therapy to a treatment site inside a patient's body, without causing imaging artifacts with the apparatus used to administer the therapy. This method includes steps that are generally consistent with the functions performed by the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

Figure 1:
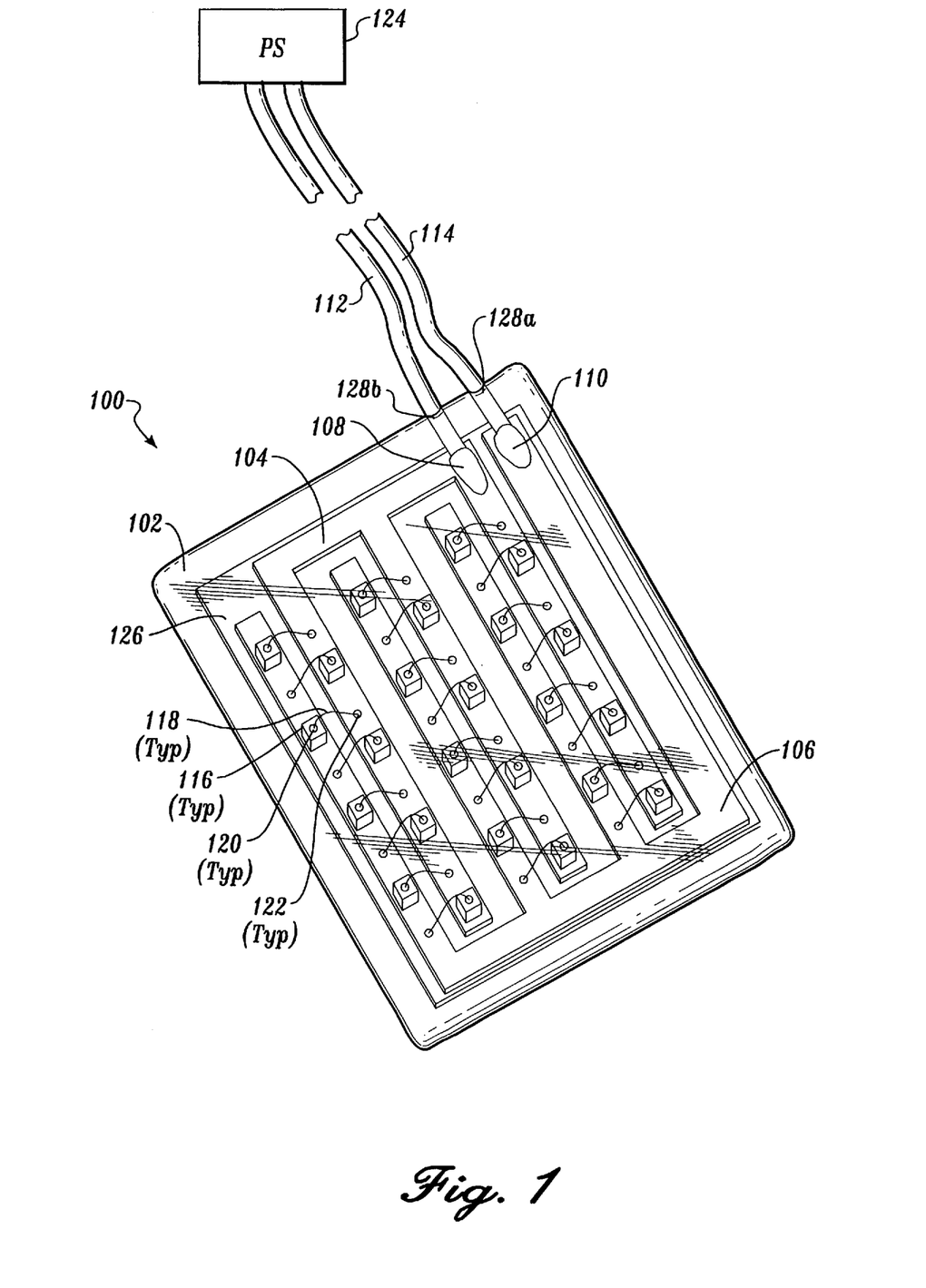
FIG. 1 is a perspective view of a PDT probe in accordance with the present invention.

With reference to FIG. 1, a PDT probe 100 embodying the present invention is illustrated having a substantially planar, rectangular shaped and electrically insulating base 126. A pair of electrically conductive, non-metallic traces 104 and 106 are applied in a grid pattern of interleaved rows on the top surface of base 126, adjacent rows being separated from each other sufficiently to avoid electrical contact between the two traces. A plurality of non-metallic LEDs 116 are mounted at spaced-apart intervals along the top surfaces of traces 104 and 106. The bottom terminal of each LED is thus in electrical contact with the trace on which it is adhesively mounted using a conductive adhesive. Typically, for each non-metallic LED 116, one end of a conductive non-metallic lead 118 is coupled by a conductive adhesive drop 120 to the top terminal of the LED, and the other end of the lead is coupled by another conductive adhesive drop 122 to the next adjacent non-metallic trace. For example, if a particular non-metallic LED 116 is positioned on the top surface of trace 106, then lead 118 would connect to trace 104.

A remotely located power supply 124 is electrically coupled by a pair of non-metallic leads 112 and 114, respectively, to traces 104 and 106 using conductive adhesive drops 108 and 110. Probe 100 is enveloped by a substantially planar rectangular enclosure 102, which is substantially transparent to light emitted by the plurality of non-metallic LEDs 116. The enclosure is preferably formed of relatively thin polymer sheets that cover the top and bottom surfaces of base 126 and are hermetically sealed around the periphery of the probe. Enclosure 102 is alternatively formed by dipping the base and other components comprising the assembly described above into a suitable liquid polymer to cover the non-metallic traces, non-metallic LEDs, and leads, which cures to produce a flexible, transparent, and biocompatible coating. Leads 112 and 114, which supply electrical power to probe 100, pass through enclosure 102, respectively, at a pair of apertures 128b and 128a. If enclosure 102 is formed by dipping the assembly into the liquid polymer, the apertures are inherently formed around these leads.

Figures 2, 3:
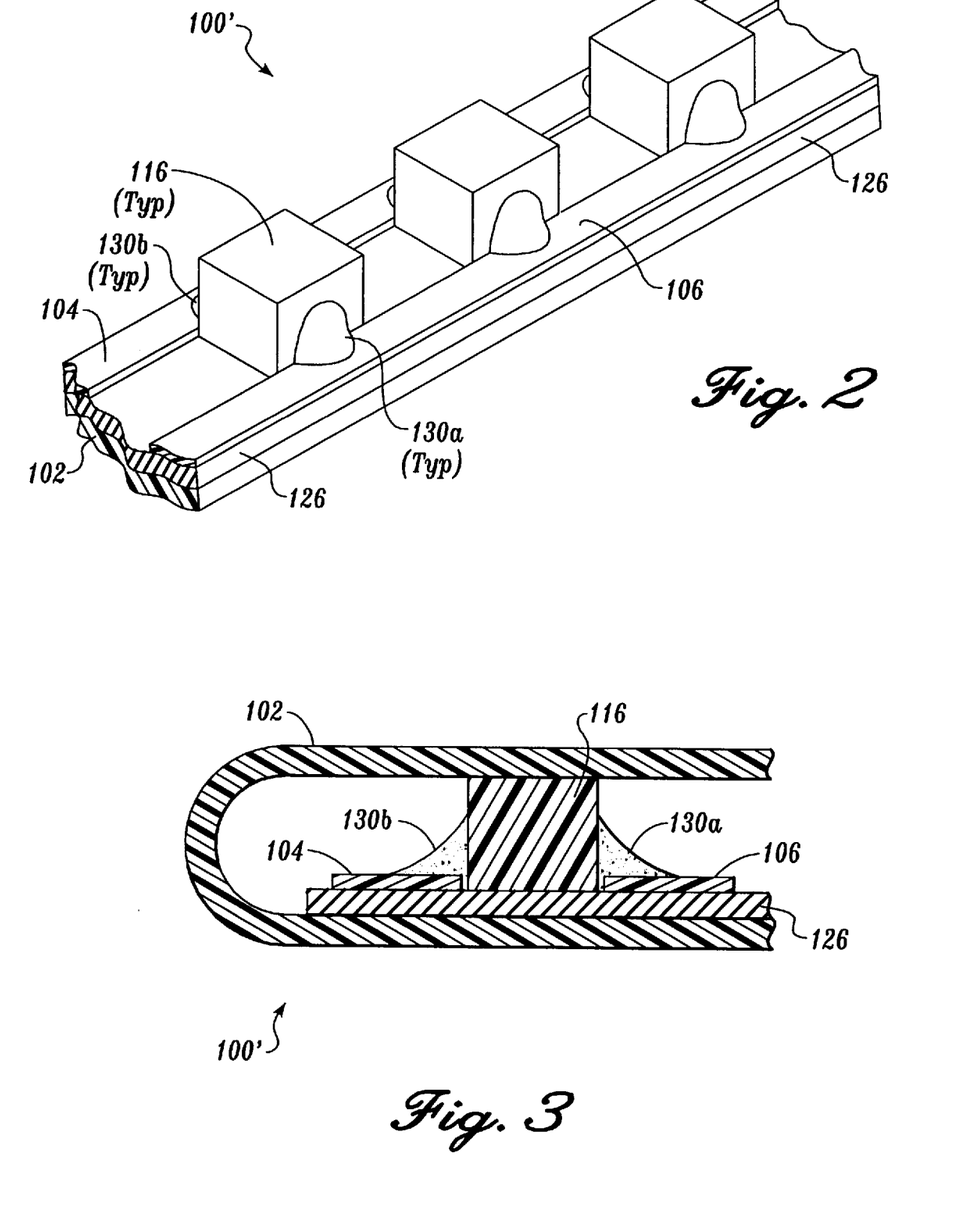
FIG. 2 is a cut-away view of the PDT probe that illustrates one embodiment for attaching non-metallic LEDs to the probe base.
FIG. 3 is a cross-sectional view of the PDT probe that further illustrates another embodiment for attaching non-metallic LEDs to the probe base.

In FIGS. 2 and 3, portions of another embodiment of the invention embodied in a probe 100' is illustrated. In this embodiment, a plurality of non-metallic LEDs 116 are mounted in a spaced apart array on base 126, between conductive non-metallic traces 104 and 106. Terminals on opposite sides of a typical non-metallic LED 116 are coupled to traces 104 and 106, respectively, by conductive adhesive drops 130b and 130a. FIG. 3 is a cross-sectional view of part of probe 100', showing the coupling of non-metallic LED 116 to traces 104 and 106 using conductive adhesive drops 130b and 130a. Also, transparent enclosure 102 encapsulates the base, non-metallic traces, and electrical components of the probe. Although not shown in FIGS. 2 and 3, traces 104 and 106 are coupled to power supply 124 in the same manner as the first embodiment (shown in FIG. 1), i.e., through non-metallic leads 112 and 114.

Figure 5:
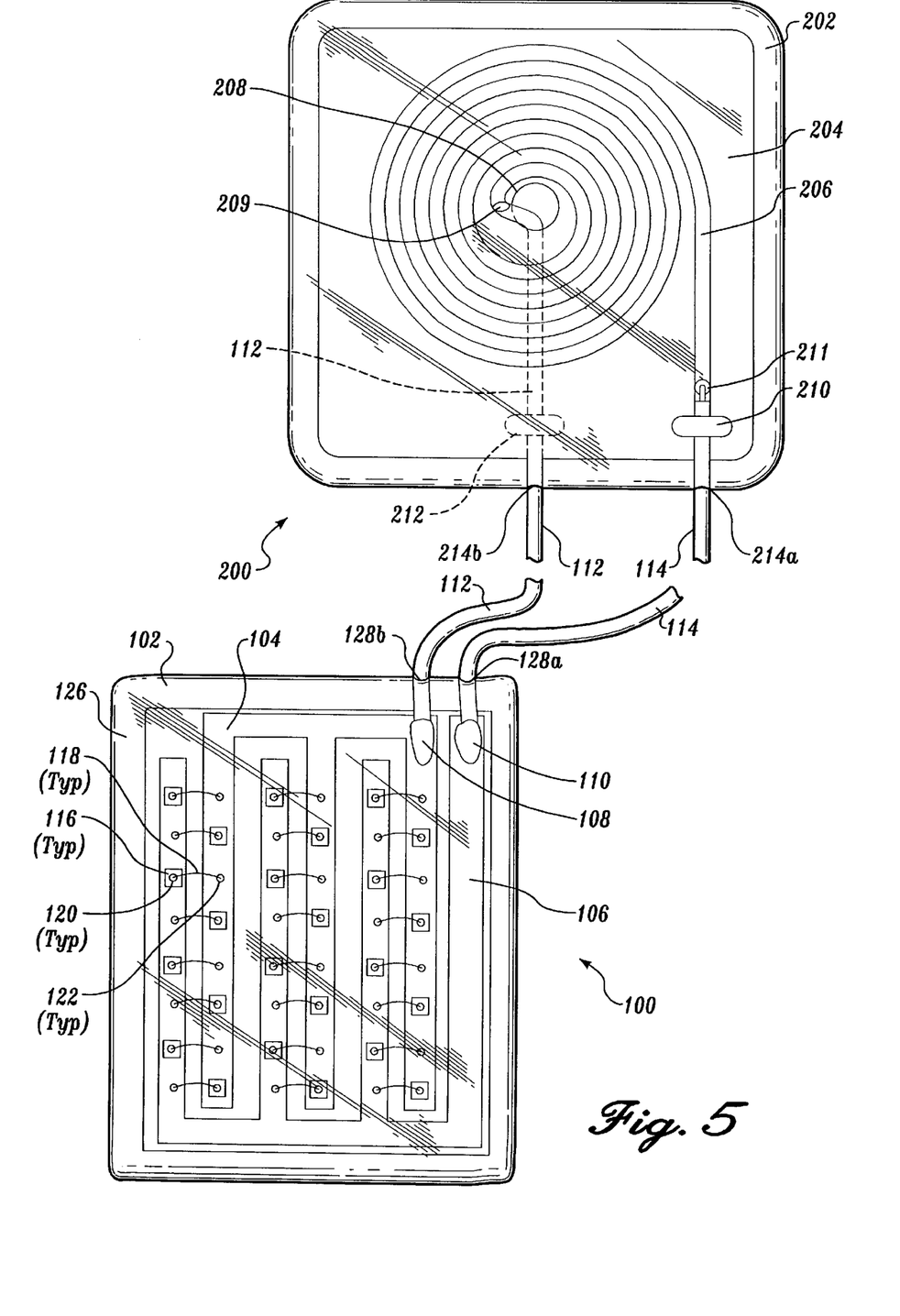
FIG. 5 is a plan view of the inductive receiver coil shown electrically coupled to the PDT probe.
Figure 6:
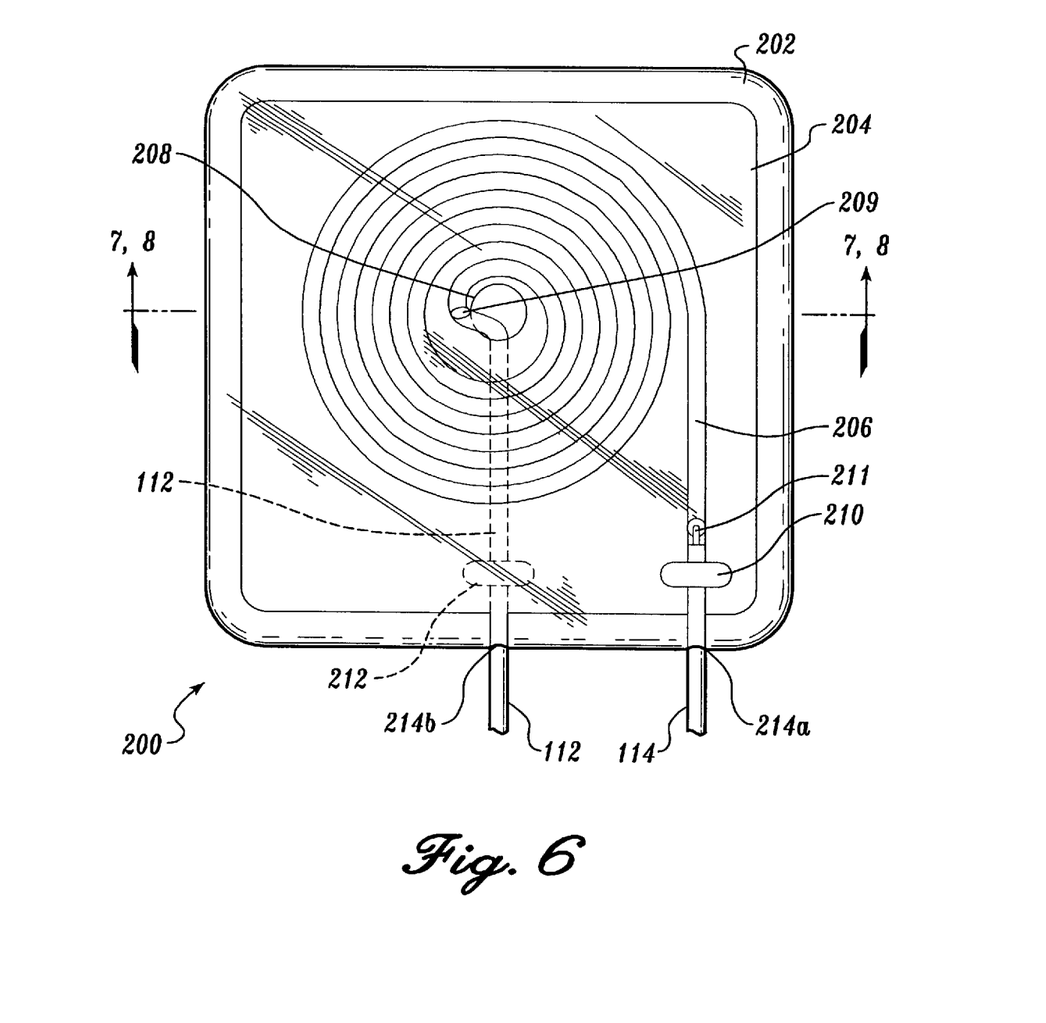
FIG. 6 is a bottom view of a non-metallic inductive receiver coil that is implanted within the patient's body to provide electrical energy to the PDT probe when energized with an external coil that is coupled to a power source.

Turning now to FIG. 5, probe 100 is shown electrically coupled to a non-metallic inductive receiver coil 200 via leads 112 and 114. FIG. 6 is a bottom view of the receiver coil. Non-metallic inductive receiver coil 200 is encapsulated in a substantially planar rectangular enclosure 202, fabricated in the same manner as enclosure 102 of probes 100 and 100'. Enclosure 202 also contains a substantially planar, rectangular shaped and electrically insulating base 204, which has an orifice 208 that is proximally located in the center of base 204. A non-metallic conductive trace 206 is applied to the top surface of base 204 and is formed in a helical spiral shape. The outer end of the spiral, non-metallic conductive trace 206 is coupled to a non-metallic lead 114 by a conductive adhesive drop 211. At the center of the helical spiral, a non-conductive lead 112 is coupled to non-metallic conductive trace 206 with a conductive adhesive drop 209 and passes through orifice 208 and across the bottom surface of base 204. A pair of adhesive attached strain reliefs 210 and 212 mount non-metallic leads 114 and 112, respectively, on the top and bottom surfaces of base 204. Electrical current induced to flow in non-metallic trace 206 is conveyed to PDT probe 100 via leads 112 and 114. These two leads enter enclosure 202 through a pair of orifices 214a and 214b disposed at the periphery of the enclosure.

Figure 7:
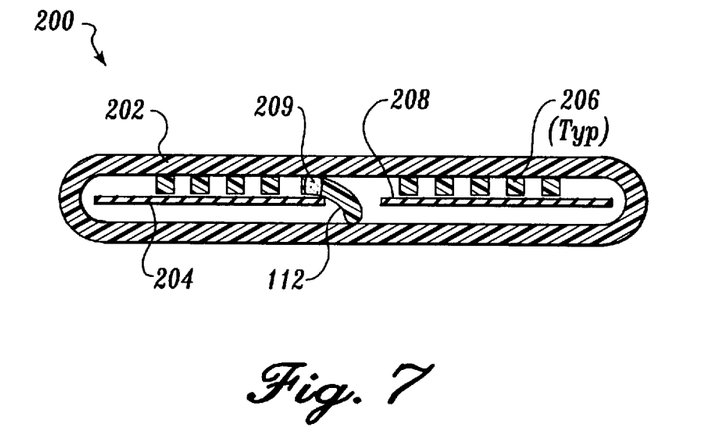
FIG. 7 is a cross-sectional view of the inductive receiver coil fabricated using non-metallic conductive traces.

Referring to FIG. 7, a cross-sectional view is shown of non-metallic inductive receiver coil 200. Optionally, non-metallic conductive trace 206 can be helically spiraled about orifice 208 on the bottom surface of base 204, so that electrical current flow through the bottom spiral is in the same direction as the helix formed on the top surface. Non-metallic conductive trace 206 is shown on the top surface of base 204, coupled to non-metallic lead 112, which passes through orifice 208 and extends along the bottom surface of base 204.

Figure 4:
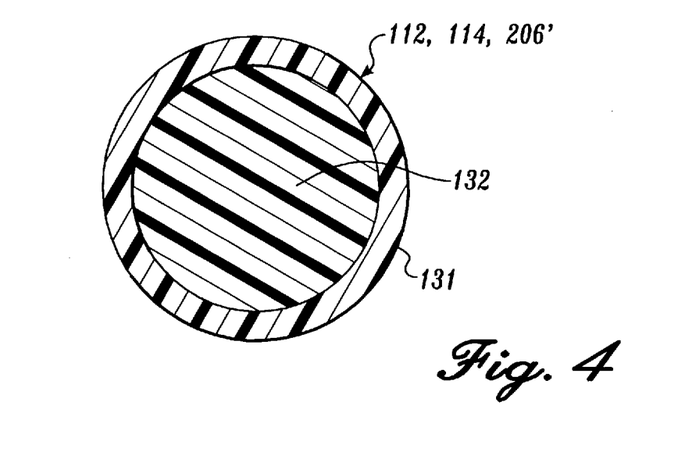
FIG. 4 is a cross-sectional view of a non-metallic, electrically conductive lead.
Figure 8:
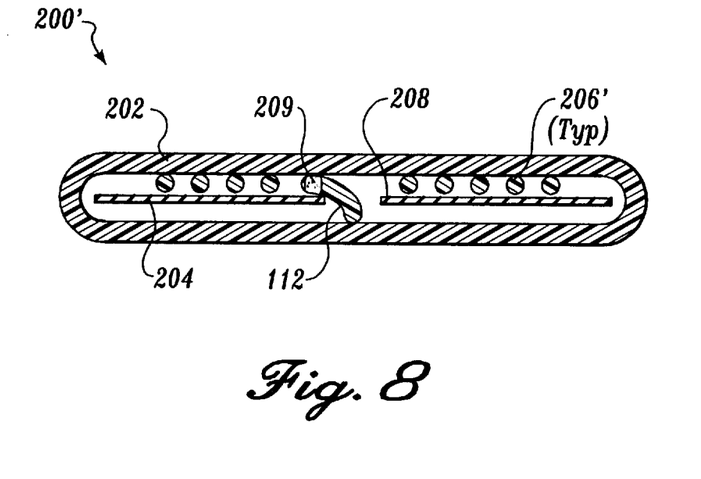
FIG. 8 is a cross-sectional view of an alternative embodiment of the inductive receiver coil fabricated using a non-metallic lead.

In FIG. 8, an alternative embodiment of a non-metallic inductive receiver coil 200' is illustrated. This embodiment includes a helical coil of a non-metallic lead 206' instead of the non-metallic conductive trace. The inner end of non-metallic lead 206' extends through orifice 208 in base 204. It will be apparent that non-metallic lead 112 or 114 can simply be extended to form the helical coil comprising non-metallic lead 206'. Non-metallic lead 206' is virtually identical in configuration to non-metallic leads 112 and 114 and includes a conducting polymer core 132 covered with an insulating polymer coating 131, as shown in FIG. 4. Since non-metallic lead 206' is insulated, it can be coiled more tightly than illustrated in the Figure, enabling more turns to be formed than shown. As the number of turns of non-metallic lead used in making receiver coil 200' increases, the coupling efficiency between the external transmitter coil and the receiver coil improves.

Figure 16:
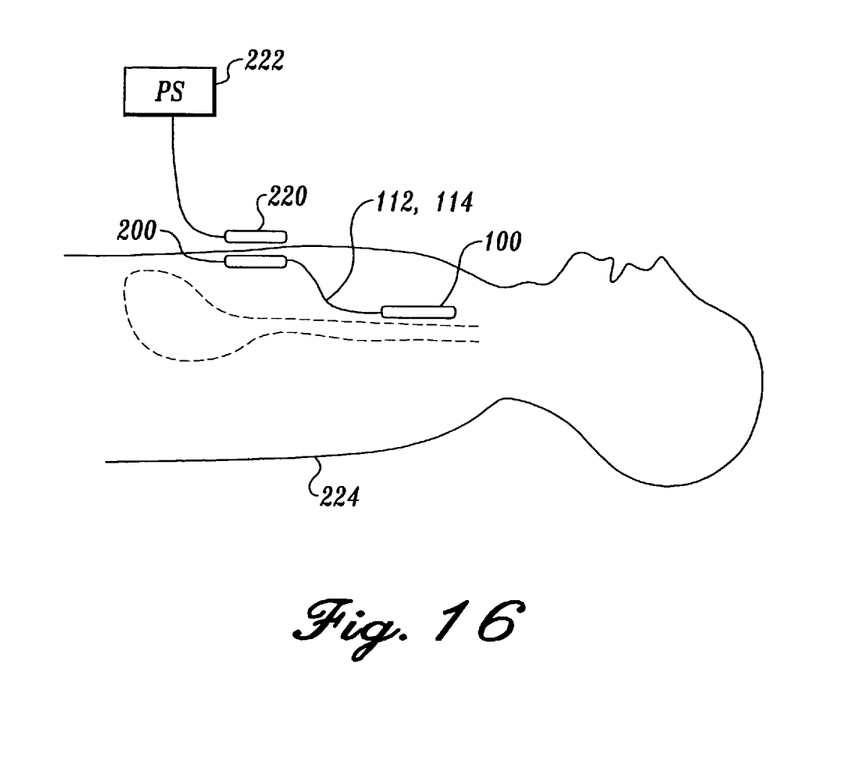
FIG. 16 is a sectional view, showing the PDT probe and the non-metallic inductive receiver coil implanted inside a patient's torso, with transmitter coil positioned above the patient's dermal layer, in proximity to the receiver coil.

In FIG. 16, to provide electrical power to energize the non-metallic LEDs on probe 100, receiver coil 200 is implanted in a patient's torso 224 at a location spaced apart from a treatment site, under the dermal layer and positioned so that the generally planar surface of the receiver coil is aligned with the epidermal surface. A corresponding transmitter coil 220 that is energized with an electrical current from an alternating current (AC) power source 222 is placed on or immediately adjacent the epidermal surface in close proximity to non-metallic receiver coil 200. The electromagnetic field generated by the current flowing in transmitter coil 220 inductively couples with non-metallic receiver coil 200, causing a corresponding AC to flow in helical non-metallic conductive trace 206 (or in coiled non-metallic lead 206'). This AC power is supplied to energize probe 100 with electrical current.

It is contemplated that the polarity of adjacent LEDs 116 can be alternated, so that a portion of the LEDs are energized by the positive half of the AC waveform and the remaining portion of the LEDs are energized by the negative half of the AC waveform. Alternatively, a non-metallic full wave rectifier circuit (not shown) can be provided as an interface between receiver coil 200 and PDT probe 100, for use in rectifying the AC signal, producing a DC signal that is applied to probe 100 via non-metallic leads 112 and 114.

In FIG. 4, a cross-sectional view of non-metallic leads 112 or 114, or lead 206' illustrates core 132 formed of a non-metallic conducting polymer, which is coated with electrically insulating polymer 131. The core is preferably extruded as a continuous strand, which is then coated with insulating polymer 131. Alternatively, core 132 may be formed of fine particles of a conducting polymer that are compressed into a strand to which the insulating polymer is applied.

In the present invention, all of the conductors used in the probe and inductive receiver coil, and all of the leads employed for coupling the probe to the receiver coil comprise a non-metallic material, such as a conducting polymer. Although there are other suitable conducting polymers available, Polypyrrole is preferred. Polypyrrole is extremely flexible and is ideal for forming traces 104 and 106, which are bonded onto base 126. Further, leads 112, 114, and 206 can employ Polypyrrole for core 132 to provide an electrical lead that is entirely non-metallic. Also, all of the exterior surfaces of the probe, the inductive receiver coil, and the non-metallic leads are made from or covered with a polymeric substance that is biologically inert, such as TEFLON™ polymer.

It is further envisioned that non-metallic inductive receiver coil 200 could be applied to the side of base 126 opposite that on which the plurality of non-metallic LEDs 116 are disposed. In this manner, a single substantially planar and rectangular shaped enclosure could fully encapsulate both non-metallic LEDs 116 and inductive non-metallic inductive receiver coil 200. The only potential disadvantage of this embodiment is that the treatment site to which the PDT is applied by the probe must be relatively close to the patient's dermal layer to inductively couple power to the non-metallic receiver coil that is part of the probe. If the treatment site is too deep within the patient's body, the integral receiver coil will be unable to efficiently inductively couple with an external transmitter coil, and inadequate power will be supplied to the LEDs on the probe.

It is also envisioned that the plurality of non-metallic LEDs 116 could be disposed on both sides of base 126 to create a double-sided embodiment of PDT probe 100. In this way, PDT could be applied simultaneously to cells on both sides of PDT probe 100 at the treatment site. However, a double-sided probe could have a greater overall thickness, increased electrical power requirements, and a higher ambient temperature during PDT than a single sided probe. Thus, a medical practitioner would have to consider at least these parameters before employing a double-sided PDT probe 100.

Additionally, the intensity of light produced by the plurality of LEDs 116 could be enhanced by the application of a reflective coating to base 126. Since base 126 can be fabricated from a suitable biocompatible plastic polymer, a material can be selected that has a relatively high light reflectance value, or a highly light reflective coating can be applied to base 126. As a result, light emitted by the plurality of LEDs 116 will be reflected toward the treatment site, so that the total illumination on the treatment site adjacent to PDT probe 100 would be increased.

Figure 9:
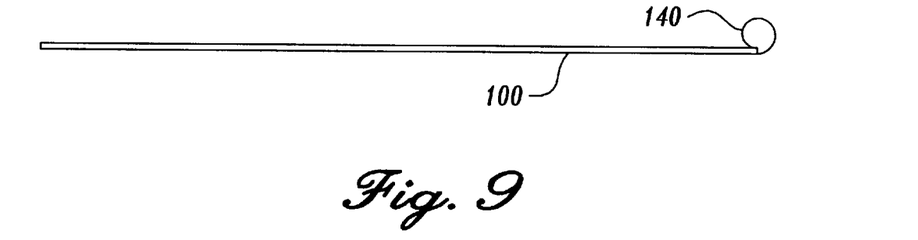
FIG. 9 is a side elevational view of a partially rolled PDT probe.
Figure 10:
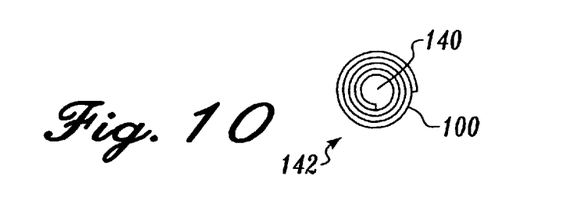
FIG. 10 is an end view of a rolled PDT probe.
Figure 11:
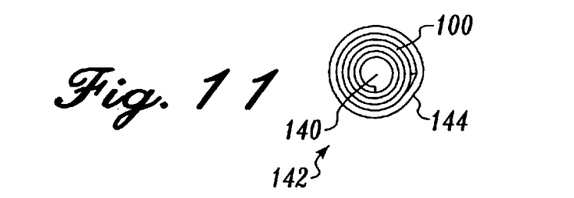
FIG. 11 is an end view of the rolled PDT probe and a retainer ring.
Figure 12:
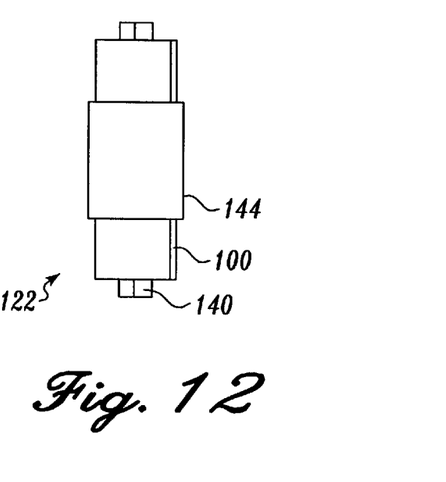
FIG. 12 is a plan view of the rolled PDT probe and the retainer ring of FIG. 14.
Figure 13:
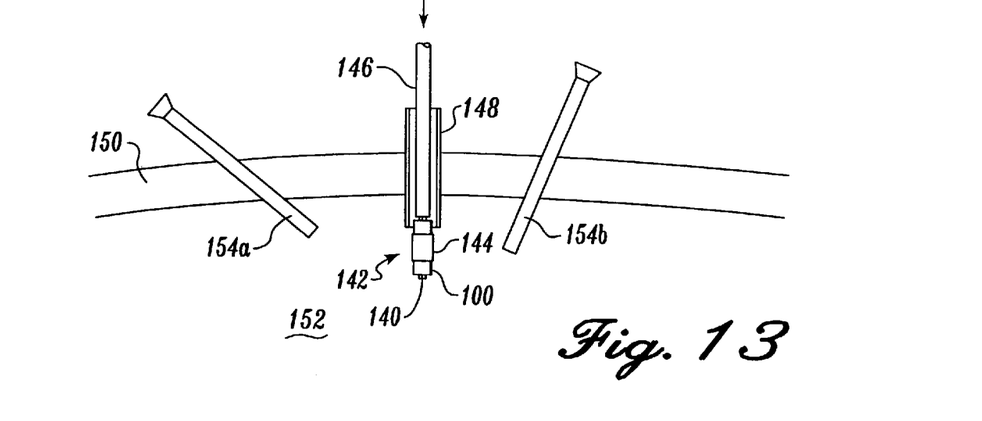
FIG. 13 is a side elevational view illustrating the rolled PDT probe being inserted into a patient's body through a laparoscopic guide tube that extends through a tissue layer.

Employing the present invention, a medical practitioner can provide PDT at a treatment site disposed within the patient's body. FIGS. 9 through 15 illustrate one method for inserting PDT probe 100 inside a patient's body using a laparoscopic procedure. In FIG. 9, PDT probe 100 is shown before it is initially rolled into concentric cylindrical layers. To facilitate rolling the flexible PDT probe 100, a cylinder template 140 is preferably used. After PDT probe 100 has been formed into a roll 142 as shown in FIG. 10, a sleeve 144 is slid over its outer surface, as shown in FIGS. 11 and 12, preventing the rolled probe from unrolling. A push rod 146 is used to insert rolled PDT probe 100 retained by sleeve 144 through a guide tube 148, as shown in FIG. 13. The guide tube is surgically positioned so that it extends through a tissue layer 150 to access an internal treatment site 152. Also illustrated in this Figure are two laparoscopic tubes 154a and 154b, both of which are inserted through tissue layer 150 at opposite sides of guide tube 148 so that their distal ends are disposed adjacent treatment site 152.

Figure 14:
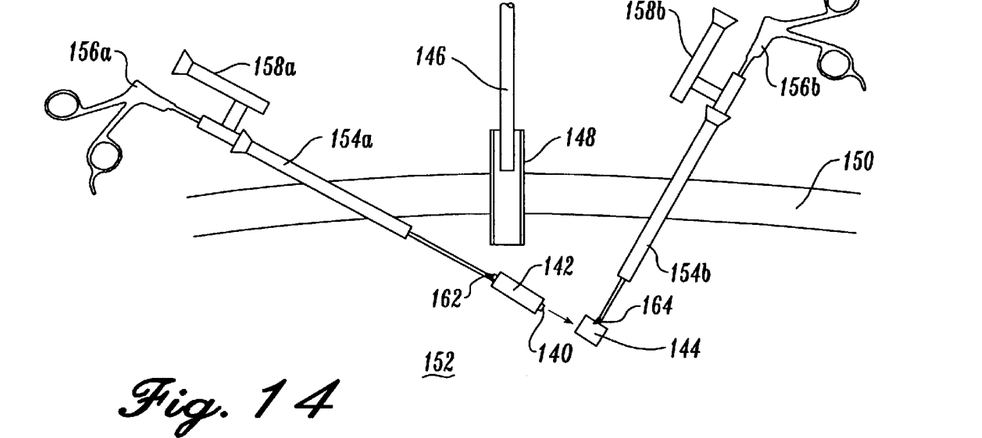
FIG. 14 is a side elevational view showing laparoscopic forceps being used to remove the retainer from the rolled PDT probe.
Figure 15:
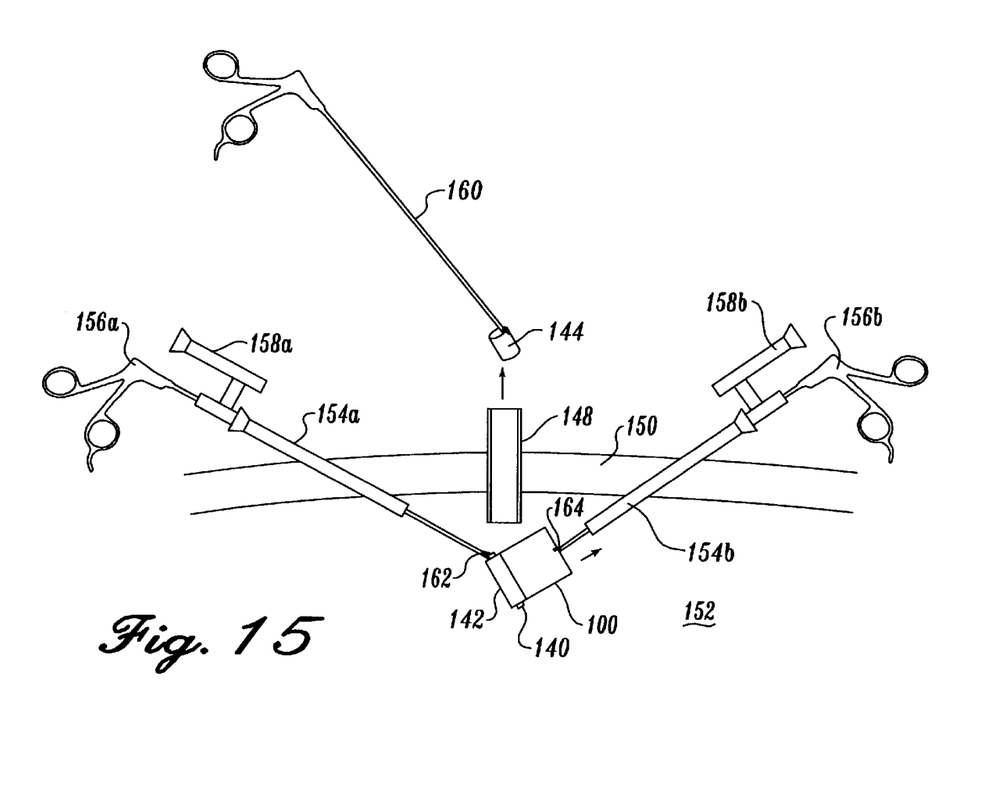
FIG. 15 is a side elevational view showing laparoscopic forceps being used to unroll the PDT probe to enable it to be used at an internal treatment site.

In FIG. 14, a pair of forceps 156a and 156b are inserted through laparoscopes 154a and 154b to enable sleeve 144 to be withdrawn from roll 142. Push rod 146 is then extracted through guide tube 148. Eye pieces 158a and 158b are provided, respectively on laparoscopes 154a and 154b to enable the operator to manipulate roll 142 and sleeve 144 during this procedure. Next, as shown in FIG. 15, forceps 160 are inserted through guide tube 148 and employed to grasp sleeve 144, withdrawing it from treatment site 152. In addition, laparoscopes 156 are used to unroll PDT probe 100 at treatment site 152. In this operation, template 140 is grasped by forceps 156a using forceps tip 162, which is disposed at the distal end of the laparoscope, while PDT probe 100 is grasped by forceps tip 164 on the other laparoscope. While not shown in the Figures, forceps 160 are then used to withdraw template 140 through guide tube 148 and PDT probe 100 is thus unrolled at the treatment site.

Additionally, a photoreactive agent is infused into the treatment site and preferentially absorbed by diseased cells that must be destroyed. The photoreactive agent has a light absorption waveband corresponding to the waveband of light emitted by the LEDs on the probe. By varying the voltage applied to the non-metallic LEDs on the probe, the medical practitioner can vary the color of light emitted to obtain the desired waveband required to effect the PDT. When the cells that have absorbed the photoreactive agent are irradiated by light emitted by the LEDs, they are destroyed by the photodynamic reaction. Thus, the medical practitioner can enhance the efficacy of a particular photoreactive agent used in the PDT by adjusting the waveband of light to achieve the optimal absorption wavelength of the photoreactive agent.

After administering PDT for a period of time, the effect on the treatment site can be determined by imaging it using a CT, MRI, or other imaging device. By inspecting the resulting images, the medical practitioner can determine whether additional PDT is required. More importantly, the probe can remain disposed at the treatment site during the imaging, without causing imaging artifacts in the CT or MRI images that might prevent the medical practitioner from properly assessing the effectiveness of the therapy.

The use of non-metallic materials in the construction of PDT probe 100 enhances the application of PDT to a treatment site by minimizing imaging artifacts in CT and MRI assessments of the progress of the therapy while the device remains in situ. Further, there are several important features of the present invention that are enabled or enhanced by the use of conducting polymers and other non-metallic materials in the construction of probes 100/100' and non-metallic inductive receiver coil 200. First, the use of a conducting adhesive to attach leads, traces, and non-metallic LEDs obviates the need for solder or metallic wire joints as taught in the prior art. The elimination of wire joints that are formed by solder and/or resistance bonding, serves to increase the overall robustness and reliability of the present invention and eliminates imaging artifacts that would be caused by using metal for interconnecting the conductors and components. Second, in the event that the integrity of enclosures 102 and/or 202 is breached and the electrical components contained therein become exposed to internal body fluids, the safety of the patient is not jeopardized. Polymeric electrical components are believed to be relatively benign biologically when compared to non-polymeric components, such as conventional LEDs made using gallium arsenide, which is an extremely toxic material. Thus, the use of polymeric electrical components increases the safety of a patient receiving PDT by reducing the likelihood of biological reactions to the components contained within PDT probes 100/100' in the event that the hermetic envelope around the probe is breached. Third, a polymeric PDT probe can be constructed in layers using thin film techniques (epitaxy), so that the overall thickness of the probe can be minimized. Fourth, the elastomeric properties or flexibility of PDT probes 100/100' are enhanced by the use of uniformly deposited thin layers of conducting polymers. Also, thin layering enables PDT probes 100/100' to be encapsulated within an enclosure that has an extremely smooth exterior surface, without adding an inordinate amount of thickness to the dimensions of the probe. Fifth, polymeric LEDs can likely be manufactured in much smaller sizes than conventional LEDs. Thus, the use of minutely sized polymeric LEDs offers further opportunities in constructing very thin probes that are flexible.

The exemplary preferred embodiment of the present invention described above is employed to deliver PDT to an internal treatment site. It is also contemplated that a probe made using non-metallic components, including a non-metallic electronic device other than an LED, in accordance with the present invention, can provide other types of medical therapy. For example, a pacemaker employing a non-metallic probe could be used for delivering cardiac pacing signals to a heart to avoid creating artifacts in images made of the heart. It is likely that relatively sophisticated electronic components of various types will be developed as conductive polymer technology matures, and use of such components will greatly expand the options for administering various types of medical therapy to a treatment site with a probe that can remain in place during imaging without creating artifacts in the resulting images. Thus, a probe for administering almost any type of medical therapy that is thus constructed without metallic components in accord with the present invention will permit imaging of the site without causing artifacts in the images.

Additionally, PDT probe 100 is not to be construed as limited to a substantially planar, rectangular shape. Instead, it is envisioned that the probe could be formed in almost any shape, such as a cylinder, a sphere, a rectangular solid, or a disk. Since polymers can be easily molded into a wide variety of shapes, the PDT probe could be custom shaped to administer the type of medical therapy required, and to conform to the specific shape of a particular treatment site within the patient's body. Consequently, a medical practitioner could select the shape of PDT probe 100 that would optimize the therapeutic effects of PDT (or other type of medical therapy) for a particular patient.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

We claim:

1. An implantable probe for use in administering a medical therapy to an internal treatment site within a patient's body, and for minimizing imaging artifacts in images produced to evaluate a condition of the internal treatment site, comprising:

(a) a non-metallic insulating base;

(b) a plurality of non-metallic conductive traces supported by the base, adapted to couple to a power supply to convey an electrical current supplied by the power supply; and (c) a non-metallic electronic component supported by the base and coupled to the conductive traces, said non-metallic electronic component being energized by the electrical current conveyed by the plurality of non-metallic conductive traces to produce the medical therapy, said implantable probe being thus configured to remain disposed at the treatment site when the treatment site is imaged, without causing an imaging artifact that would obscure the treatment site in said images.

2. The implantable probe of claim 1, wherein the conductive traces comprise a conductive polymer.

3. The implantable probe of claim 1, wherein the non-metallic electronic component comprises a light emitting device.

4. The implantable probe of claim 1, wherein the non-metallic electronic component comprises a light emitting polymer.

5. The implantable probe of claim 1, wherein the non-metallic electronic component comprises an organic film light emitting device.

6. The implantable probe of claim 1, further including an envelope comprising a biocompatible material for hermetically enclosing the base, the plurality of non-metallic conductive traces, and the non-metallic electronic component.

7. The implantable probe of claim 1, wherein the base and the conductive traces are substantially flexible.

8. The implantable probe of claim 1, wherein the non-metallic base is substantially light reflective.

9. The implantable probe of claim 1, further comprising a plurality of non-metallic electronic components, wherein the plurality of non-metallic electronic components are disposed on opposite surfaces of the non-metallic base.

10. The implantable probe of claim 1, wherein the implantable probe has a shape generally corresponding to one of a cylinder, a sphere, a rectangular sheet, a disk, and a rectangular solid.

11. The implantable probe of claim 1, further comprising a non-metallic receiver coil that is implantable within the patient's body and which is connected to the non-metallic conductive traces through non-metallic conductive leads, said non-metallic receiver coil being adapted to inductively couple to an external transmitter coil energized with a time varying electrical current from an external power source, the electrical current that is thereby induced in said non-metallic receiver coil energizing said non-metallic electrical component.

12. A method for providing a medical therapy to a treatment site inside a patient's body, while avoiding artifacts in images made of the treatment site by apparatus used to administer the medical therapy, comprising the steps of:

(a) providing an implantable probe that comprises non-metallic components, including a plurality of non-metallic conductors for conveying an electrical current, and a non-metallic electrical component coupled to the non-metallic conductors and energized by the electrical current to provide the medical therapy;

(b) placing the implantable probe at the treatment site;

(c) energizing the non-metallic electrical component to administer the medical therapy to the internal treatment site; and (d) imaging the treatment site while the implantable probe is disposed adjacent thereto, use of said non-metallic components in the implantable probe substantially eliminating artifacts in images produced thereby.

13. The method of claim 12, wherein the plurality of non-metallic conductors comprise a conductive polymer.

14. The method of claim 12, wherein the non-metallic electrical component comprises a plurality of light emitting devices disposed in an array within the implantable probe.

15. The method of claim 12, wherein the non-metallic electrical component comprises a light emitting polymer.

16. The method of claim 12, wherein the non-metallic electrical component comprises an organic film light emitting device.

17. The method of claim 12, further comprising the step of enclosing the non-metallic conductive traces and non-metallic electrical component within a hermetically sealed biocompatible envelope.

18. The method of claim 12, further comprising the step of evaluating the condition of the treatment site based upon the images produced, and as a function of said evaluation, selectively energizing the non-metallic electrical component to administer additional medical therapy to the treatment site.

19. The method of claim 12, wherein the step of imaging includes the step of using one of a computed tomography apparatus and a magnetic resonance imaging apparatus to produce the images of the treatment site.

20. The method of claim 12, wherein the non-metallic conductors are substantially flexible.

21. The method of claim 12, wherein the non-metallic base is substantially light reflective.

22. The method of claim 12, further comprising the step of providing a plurality of non-metallic electronic devices disposed on opposite sides of the non-metallic base.

23. The method of claim 12, wherein the implantable probe has a shape that is generally like one of a cylinder, a sphere, a rectangular sheet, a disk, and a rectangular solid.

24. The method of claim 12, further comprising the steps of:

(a) implanting a non-metallic receiver coil within the patient's body;

(b) connecting the non-metallic receiver coil to the non-metallic electrical component through non-metallic conductive leads that are connected to the non-metallic conductors; and (c) inducing an electrical current to flow in the non-metallic receiver coil with an external transmitter coil that is coupled to an external power source, for energizing the non-metallic electrical component.

25. An implantable probe for use in administering light therapy to an internal treatment site within a patient's body, said apparatus minimizing imaging artifacts in images produced to evaluate a condition of the treatment site in response to the light therapy, comprising:

(a) a non-metallic insulating base;

(b) a pair of non-metallic conductive traces supported by the base, adapted to couple to a power supply and convey an electrical current provided by said power supply; and (c) a non-metallic light source supported by the base and coupled to the conductive traces, said non-metallic light source being energized by the electrical current conveyed by the non-metallic conductive traces to produce light employed for the light therapy, said implantable probe being thus configured to remain disposed at the treatment site while the treatment site is imaged without causing an imaging artifact that would obscure the treatment site in images produced thereby.

26. A method for providing light therapy to a treatment site inside a patient's body, without causing artifacts in images made of the treatment site while apparatus used to administer the light therapy remains at the treatment site, comprising the steps of:

(a) providing an implantable probe that comprises non-metallic components, including a plurality of non-metallic conductors for conveying an electrical current, and a non-metallic light source that is energized by the electrical current conveyed by the non-metallic conductors;

(b) positioning the implantable probe at the treatment site;

(c) applying a photoreactive agent to the treatment site, said photoreactive agent being preferentially absorbed by tissue at the treatment site and having an absorption waveband substantially within a waveband of light produced by the light source;

(d) energizing the light source with the electrical current to illuminate the treatment site for a period of time; and (e) imaging the treatment site while the implantable probe remains disposed adjacent thereto, use of said non-metallic components in the implantable probe minimizing creation of artifacts in images produced thereby.

* * * * *